US012629214B2

(12) United States Patent
Tille

(10) Patent No.: US 12,629,214 B2
(45) Date of Patent: May 19, 2026

(54) DEVICES AND METHODS FOR IMAGING AND SURGICAL APPLICATIONS

(71) Applicant: Leica Microsystems CMS GmbH, Wetzlar (DE)

(72) Inventor: Sebastian Tille, Wetzlar (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 324 days.

(21) Appl. No.: 18/063,702

(22) Filed: Dec. 9, 2022

(65) Prior Publication Data

US 2023/0181262 A1     Jun. 15, 2023

(30) Foreign Application Priority Data

Dec. 10, 2021     (DE) .......................... 102021132637.0

(51) Int. Cl.
*A61B 34/20*          (2016.01)
*A61B 90/00*          (2016.01)
(52) U.S. Cl.
CPC ............ *A61B 34/20* (2016.02); *A61B 90/361* (2016.02)
(58) Field of Classification Search
CPC ....... A61B 34/20; A61B 90/361; A61B 90/20; A61B 2090/364; G16H 20/40; G16H 30/20; G16H 30/40
See application file for complete search history.

(56) References Cited

U.S. PATENT DOCUMENTS

| | | | | |
|---|---|---|---|---|
| 2010/0149183 A1* | 6/2010 | Loewke | ............... | G06V 20/693 |
| | | | | 345/424 |
| 2012/0033933 A1* | 2/2012 | Suzuki | .................... | G11B 27/28 |
| | | | | 386/230 |
| 2018/0122333 A1* | 5/2018 | Horiike | .................... | H04N 5/64 |
| 2019/0279765 A1 | 9/2019 | Giataganas et al. | | |
| 2020/0273581 A1* | 8/2020 | Wolf | ...................... | G16H 40/63 |
| 2020/0360100 A1* | 11/2020 | Mantri | .................... | A61B 34/25 |
| 2021/0313052 A1* | 10/2021 | Makrinich | ............. | G11B 27/34 |
| 2022/0061927 A1* | 3/2022 | Sramek | .................. | B25J 9/1689 |
| 2023/0285081 A1* | 9/2023 | Wagner | .................. | A61B 34/10 |

FOREIGN PATENT DOCUMENTS

| | | |
|---|---|---|
| DE | 102015219971 A1 | 4/2017 |
| WO | 2019079430 A1 | 4/2019 |

* cited by examiner

*Primary Examiner* — Alexei Bykhovski
(74) *Attorney, Agent, or Firm* — 2SPL Patent Attorneys PartG mbB; Yong Beom Hwang

(57)          ABSTRACT

A surgical imaging device is disclosed. The surgical imaging device configured for acquiring a plurality of images of a surgical site, stitching a map of the surgical site using the plurality of images, and displaying the map and a real-time image acquired by the surgical imaging device. Furthermore, a device for providing a video of a surgery is disclosed. The device is configured for outputting a map of a surgical site, and outputting a line on the map which connects a plurality of positions on the map. The positions each correspond to respective scenes of a video of a surgery of the surgical site.

18 Claims, 3 Drawing Sheets

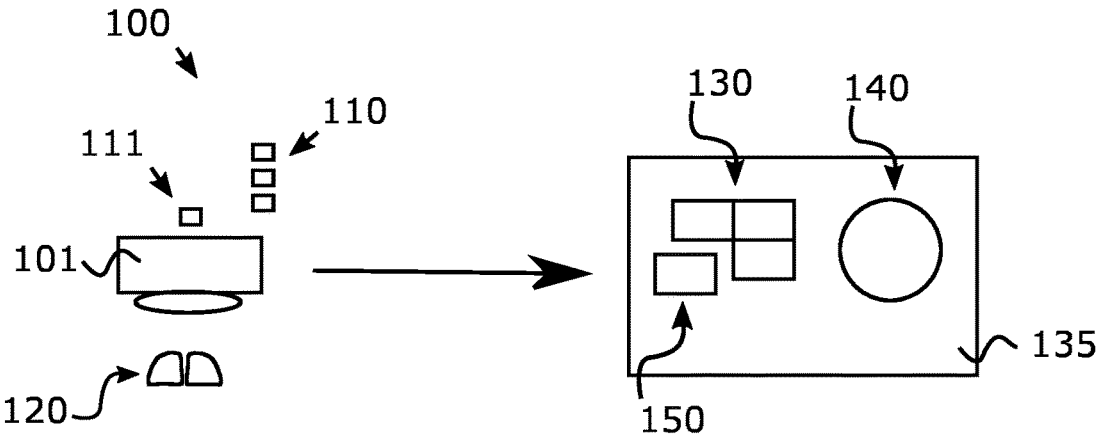
Fig. 1A
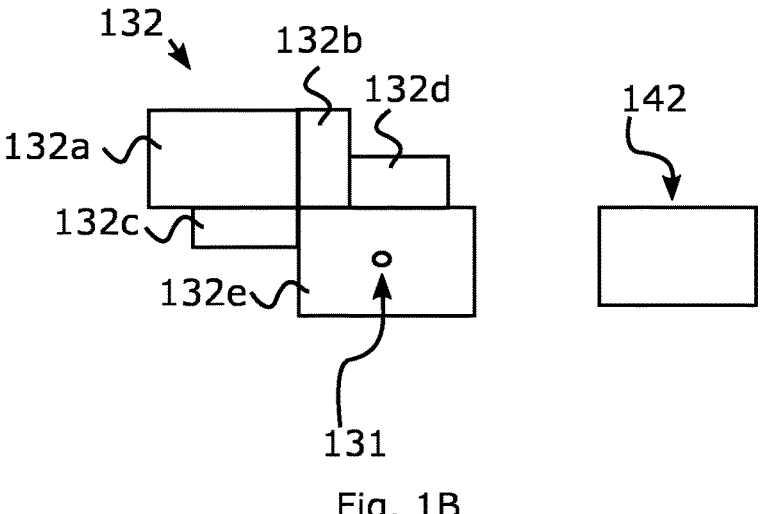
Fig. 1B
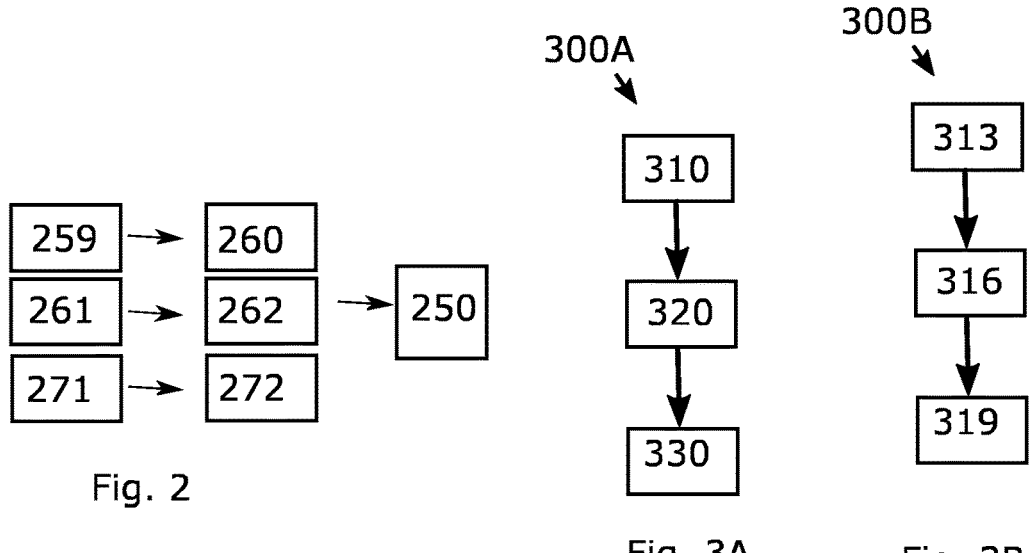
Fig. 2
Fig. 3A
Fig. 3B

900

935

950

970

980

901

910    920

1000

1010

1020

1030

1040

1050

DEVICES AND METHODS FOR IMAGING AND SURGICAL APPLICATIONS

TECHNICAL FIELD

Examples disclosed herein relate to imaging, image processing, and/or video playback related to surgical applications.

BACKGROUND

Optical surgical microscopes are used for a wide range of surgical procedures. Microscopes can provide a live magnified view of selected parts of the surgical field to the surgeon. The magnified view may cover only a part of the surgical field, so that whenever a different area needs to be viewed, as the surgical procedure requires, the microscope and/or its field of view may be moved, potentially combined with a change of the magnification (also called zoom) level, and/or an adjustment of the focus of the optics to re-establish a sharp image.

Modern surgical microscopes also allow the view of the optical image to be augmented, e.g. by an overlay with additional information, such as data acquired and processed pre-operatively also using other imaging modalities, such as magnet resonance or computer tomography or ultrasound. Moreover, the use of digital cameras attached to the microscope enable outputting the microscopic image onto computer screens which can give the whole team in the operating room (OR) and beyond the chance to follow the operation, seeing what the surgeon is seeing.

SUMMARY

It may be desirable to improve the ability of healthcare professionals in the OR to maintain a sense of orientation and correct interpretation of the perspective of images during surgery. It may also be desirable to support the surgeon in efficiently navigating across the surgical field with little effort and to reduce user interactions with the microscope, e.g. avoiding the need for changing position, zoom, and/or focus of the microscope optics. It may be possible to increase the efficiency and reduce the time of the procedure, and thus improve chances for a better patient outcome It may furthermore be desirable to improve the navigability of playback of recorded videos of surgeries, e.g. when viewed post-operatively for an improved training and education experience.

Herein is disclosed a surgical imaging device as in appended claim 1.

A surgical imaging device is disclosed, which is configured for: acquiring a plurality of images of a surgical site; stitching a map of the surgical site using the plurality of images; and outputting and/or displaying the map and a real-time image acquired by the surgical imaging device. Such a device can aid in the navigability of the surgical site to have a stitched map and real-time image being available.

Herein is disclosed a surgical imaging device in which the stitching includes adding an added region to the map, wherein the plurality of images includes the added region. Such a device can aid in the navigability of the surgical site to have a stitched map and real-time image being available.

Herein is disclosed a surgical imaging device configured such that the added region (which is added to the map) is at least one of: a previously unmapped region, an image with different resolution than a previous resolution of the map, or an image taken at a different focus position than the so far contained in the existing stitched map. Such a device can aid in the navigability of the surgical site to have a stitched map and real-time image being available.

Herein is disclosed a surgical imaging device, configured for: acquiring new images, in real time, to add to the plurality of images. Such a device can aid in the navigability of the surgical site, e.g. by increasing the mapped area.

Herein is disclosed a surgical imaging device, further configured for: selecting the added region from the plurality of images. Such a device can aid in the navigability of the surgical site, e.g. by increasing the mapped area using added regions for enlarging and/or providing enhanced resolution to the map.

Herein is disclosed a surgical imaging device, further configured for: comparing the added region of the plurality of images to the map before identifying the added region of the plurality of images as being unmapped, identifying the added region of the plurality of images as being unmapped, and subsequently adding the added region to the map. Such a device can aid in the navigability of the surgical site, e.g. by increasing the mapped area.

Herein is disclosed a surgical imaging device, further configured for: updating the map using an updated image acquired from the apparatus. Such a device can aid in the navigability of the surgical site, e.g. by providing enhanced resolution to the map and/or allowing for changed features and/or regions of the surgical site to be included into the map.

Herein is disclosed a surgical imaging device, further configured for: acquiring at a changed focus or acquiring at a changed zoom, and subsequently, updating the map using the updated image acquired at the changed focus or changed zoom. Such a device can aid in the navigability of the surgical site, e.g. by providing enhanced resolution and/or depth of field to the map.

Herein is disclosed a surgical imaging device, further configured for: storing a position of a point of the map based on a user input; and marking at least one of the map or the real time image based on the position. Such a device can aid in the navigability of the surgical site, e.g. by facilitating the recognition of points of particular interest in the surgical site.

Herein is disclosed a surgical imaging device, further configured for: associating a pre-operative image with the position and/or a point on the map. Such a device can aid in the navigability of the surgical site, e.g. by facilitating the recognition of points of particular interest in the surgical site.

Herein is disclosed a surgical imaging device, further configured for: labeling the position with a user selected label. Such a device can aid in the navigability of the surgical site, e.g. by facilitating the recognition of points of particular interest in the surgical site.

Herein is disclosed a surgical imaging device, further configured for: marking the map or the real time image with a pointer to indicate at least one of a direction and a distance to the position. Such a device can aid in the navigability of the surgical site, e.g. by facilitating the user's orientation in the map.

Herein is disclosed a surgical imaging device, further configured for displaying the pointer at an edge of the real time image. Such a device can aid in the navigability of the surgical site, e.g. by facilitating the user's orientation in the map, e.g. while leaving the live image relatively unobstructed.

Herein is disclosed a surgical imaging device, further configured for using zoom settings or using focus settings to determine parameters of the added region; wherein optionally the parameters include at least one of a position of the added region in the map, a dimension of the added region. Such a device can aid in the navigability of the surgical site, e.g. by providing further orienting and/or explanatory information regarding the parts of the map, e.g. position, focus, zoom.

Herein is disclosed a surgical imaging device, further configured such that: acquiring the plurality of images includes: acquiring a stack of images at different focuses at a given position. Such a device can aid in the navigability of the surgical site, e.g. by providing enhanced resolution and/or depth of field to the map.

Herein is disclosed a device for providing a video of a surgery, configured for: outputting a map of a surgical site, and outputting a line on the map which connects a plurality of positions on the map, wherein the positions each correspond to respective scenes of a video (e.g. a recorded video) of a surgery of the surgical site. Such a device can aid in the navigability of the surgical video, such as in quickly finding a recorded scene for playback.

The device can be such that each scene includes a first frame which is the first frame of a plurality of sequentially recorded frames at the position corresponding to the scene. Such a device can aid in the navigability of the surgical video.

The device can be configured to receive a user selection of a selected position of the plurality of the positions, and play the video beginning at a first frame of the scene which corresponds to the scene corresponding to the selected position. Such a device can aid in the navigability of the surgical video.

The device can be further configured for: outputting a label at one of the positions, wherein the label corresponds to a frame of the video, wherein the label is selectable by the user for playing the video beginning at the frame of the video which corresponds to the label. Such a device can aid in the navigability of the surgical video, e.g. by enabling positions of interest of the map to correlate to a video and a possibly descriptive label which may aid in informing a user of the content of the video that corresponds to the label and/or position.

The device can be further comprising a timeline bar which is displayed, and a slider, in the timeline bar, wherein the slider is configured for user input for selecting a frame of the video. Such a device can aid in the navigability of the surgical video, e.g. by enabling visualization of temporal information for navigating the video of the procedure.

The device can be further configured for: sequentially outputting frames of a surgical video which includes a plurality of scenes, wherein each scene is recorded at a corresponding position of a surgical site, outputting a marker for marking the line, receiving user input for moving the marker on the line to a selected position corresponding to a selected scene of the plurality of scenes, and playing the surgical video beginning at a first frame of the selected scene. Such a device can aid in the navigability of the surgical video.

The device can be further configured for: moving the marker to a subsequent scene when the surgical video finishes playing a previous scene and begins playing the subsequent scene. Such a device can aid in the navigability of the surgical video.

Herein is disclosed an image processing device, configured for: recording a video with a surgical imaging apparatus, determining a plurality of scenes of the video, each scene having a first frame of a plurality of sequentially recorded frames of the video, the sequentially recorded frames being recorded at a position of a surgical site corresponding to the scene, determining a timeline of the surgery, the timeline including: a sequence of the plurality of scenes. Such a device can aid in the navigability of the surgical video.

The image processing device can be such that the first frame of each scene is determined by at least one of: a change of the field of view of the surgical imaging apparatus, or a user input.

Such a device can aid in the navigability of the surgical video, e.g. by providing scene(s) which can aid in dividing to aid in the navigation of the video.

The image processing device can be further configured for: adding a corresponding label to each scene, wherein each corresponding label is determined by at least one of: a timestamp, a duration of the scene, or a user input. Such a device can aid in the navigability of the surgical video, e.g. by providing labels which can aid in informing a user of the scenes.

The image processing device can be further configured for labeling the map with a plurality of indicators which indicate the scenes. Such a device can aid in the navigability of the surgical video, e.g. by providing labels which can aid in informing a user of the scenes.

Herein is disclosed a method of imaging for surgery, comprising: acquiring a plurality of images of a surgical site; stitching a map of the surgical site using the plurality of images; displaying the map and a real-time image acquired by the surgical imaging device. Such a method can aid in the navigability of the surgical site.

Herein is disclosed a method of surgery playback, comprising: outputting a map of a surgical site, and outputting a line on the map which connects a plurality of positions on the map, wherein the positions each correspond to respective scenes of a video of a surgery of the surgical site. Such a method can aid in the navigability of the surgical video.

Herein is disclosed a method of recording a surgery, comprising: recording a video with a surgical imaging apparatus, determining a plurality of scenes of the video, each scene having a first frame of a plurality of sequentially recorded frames of the video, the sequentially recorded frames being recorded at a position of a surgical site corresponding to the scene, determining a timeline of the surgery, the timeline including: a sequence of the plurality of scenes. Such a method can aid in the navigability of the surgical site.

Herein is disclosed a computer program comprising instructions to execute the method of any one or more of the methods disclosed herein. Such a method can aid in the navigability of the surgical site and/or video.

SHORT DESCRIPTION OF THE FIGURES

Some examples of apparatuses and/or methods will be described in the following by way of example, and with reference to the accompanying figures, in which FIG. 1A illustrates a surgical imaging device, according to embodiments described herein;

FIG. 1B illustrates a map and real time image, according to embodiments described herein;

FIG. 2 illustrates a determination of a region to be added to a map of a surgical site, according to embodiments described herein;

FIG. 3A shows a method of imaging for surgery, according to embodiments described herein;

FIG. 3B shows a method of imaging for surgery, according to embodiments described herein;

DETAILED DESCRIPTION

Figures 4, 5, 6, 7, 8:
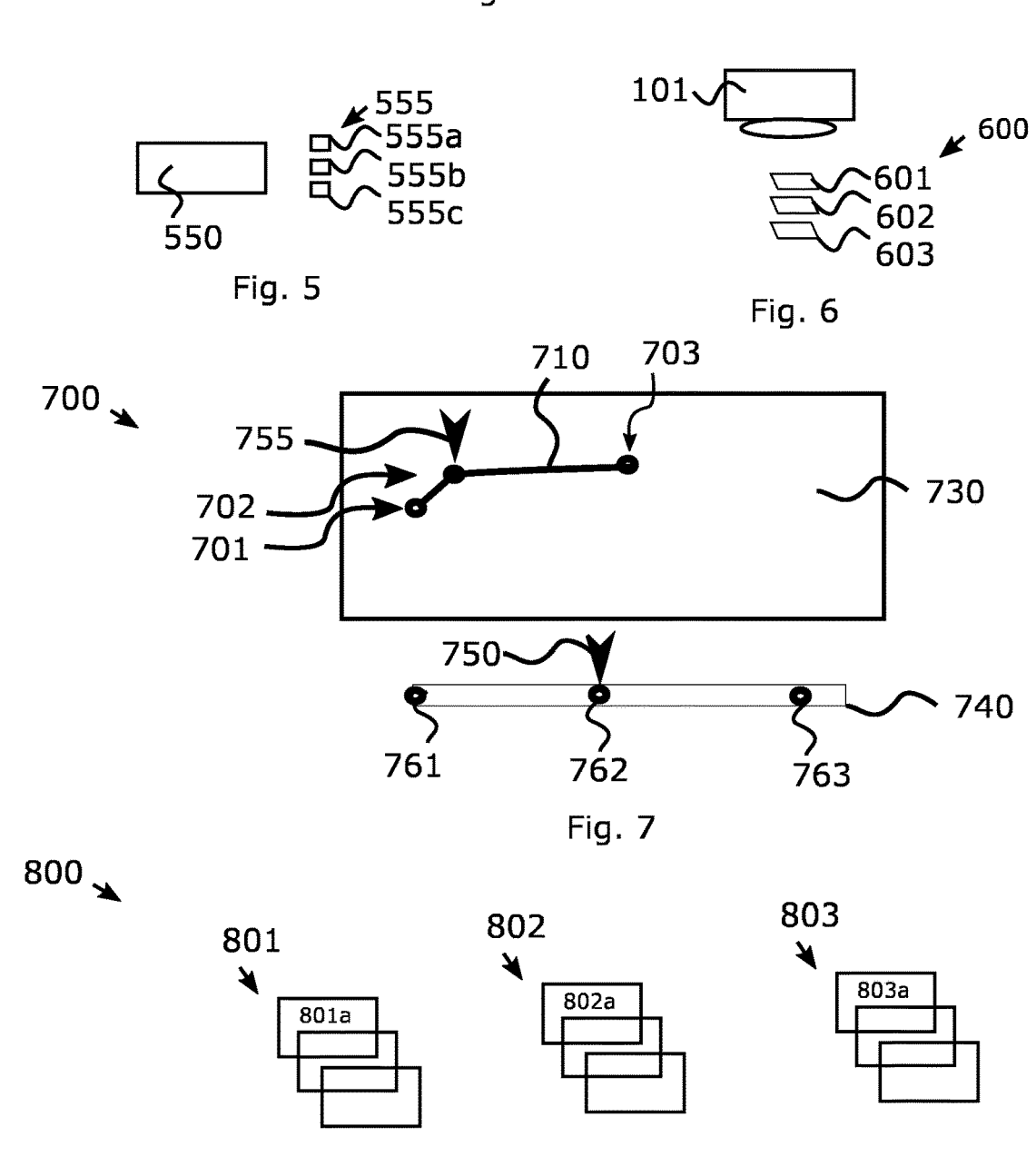
FIG. 4 illustrates a device output, according to embodiments described herein.
FIG. 5 illustrates an added region and associated parameters, according to embodiments described herein.
FIG. 6 illustrates a stack of images, according to embodiments described herein.
FIG. 7 illustrates a device for providing a video of a surgery, according to embodiments described herein.
FIG. 8 illustrates a video, according to embodiments described herein.

Various examples will now be described more fully with reference to the accompanying drawings in which some examples are illustrated. In the figures, which are not to be assumed to be to scale, the thicknesses of lines, layers and/or regions may be exaggerated for clarity.

As used herein, the term "and/or" includes any and all combinations of one or more of the associated listed items and may be abbreviated as "/". Herein, a trailing "(s)" indicates one or more; for example remote device(s) indicates one or more remote devices.

Herein, a real time image can be an image of a surgical site which is output for display without delay. Real time images can be intended for visualizing surgical sites while performing a surgery, for example.

FIG. 1A illustrates a surgical imaging device. The device 100 can acquire images 110 of a surgical site 120. The device 100 can optionally record a surgery, e.g. make a video recording of the surgery or parts of the surgery. The video can be played back on the imaging device 100 or some other device such as a playback device.

New images 111 can be acquired by the imaging device 100 in real time to add to the acquired images 110 and/or stitch to the map 130. The device can output a real time image 140 acquired by the device 100. The device 100 can, using the images, stitch a map 130 together. The map 130 and/or real-time image 140 can be outputted simultaneously, such as to one or more displays 135. Surgeons' and other professionals' physical orientation in the surgical site can be aided by having the map 130 and real time image 140 displayed.

The device 100, as shown in FIG. 1A, can include a detector 101 such as a camera for acquiring the images 110. The device 100 can include one or more processors, memory devices, and other components for imaging, image processing, and the like.

The map 130 can be determined from multiple images 110, which can aid a surgeon or other medical professional in navigating the surgical site 120. For example, the surgical imaging device can provide highly detailed images 110 from multiple positions in the surgical site 120. When a surgeon changes position, it is sometimes difficult to return easily to a previous position (such as a previously marked or imported position). A map 130, particularly one formed by stitching together multiple images 110, can aid a surgeon in navigating a surgical site 120, e.g. by providing an image of an area which is larger than a single field of view of the detector 101.

Imaged regions may be added to the map 130 in real time as images 110 are acquired. Alternatively/additionally, the device 100 can acquire new images 111 in real time which can be added to the images 110. Regions of the images 110 can be added to the map.

Stitching the map 130 together can include adding an added region 150 to the map 130. For example, the device 100 can acquire a new image 111 at a region of the surgical site 120 which has not previously been stitched into the map 130. The added region 150, which can be in one or more of the images 110, can be added to the map 130. It is useful for the device 100 to be able to continuously add more regions to the map 130 in order to generate a map 130 of greater area or increased resolution of the surgical site 120.

The display 135 of FIG. 1A shows a map 130 which can be understood to have been stitched from four images including the added region 150. A skilled person understands that the stitched regions of images can be any shape. Furthermore, the real time image 140 can take on a different shape than shown in FIG. 1A, e.g. a rectangle.

FIG. 1B illustrates a map and real time image. For example, the map 132 and real time image 142 can be output and/or displayed simultaneously. FIG. 1B illustrates multiple regions 132*a*, 132*b*, 132*c*, 132*d*, 132*e* of the map 132. The map 130 can be formed by stitching regions 132*a*, 132*b*, 132*c*, 132*d*, 132*e* together. Each region 132*a*, 132*b*, 132*c*, 132*d*, 132*e* may be at least part of one or more previously captured images 110. FIG. 1B highlights that the map 132 can take on an irregular shape, e.g. as determined by the area captured by the images 110 used to stitch the map 132.

FIG. 1B also illustrates, in the map 132, the current position 131 of the center of the field of view of the detector 101. The real time image 142 can be a real time image of centered at the current position 131. As a nonlimiting example to aid in understanding, the images 110 acquired could have sequentially included the regions 132*a*, 132*b* (by having moved to the right), 132*c* (by having moved subsequently down), 132*d* (by having moved subsequently right), and 132*e* (by having moved subsequently right and down). The map 132 can be stitched by using regions from images acquired sequentially starting from an image which included the first region 132*a*, in this example. Overlapping regions are not explicitly shown in FIG. 1B. However, the identification of overlapping regions, e.g. by comparing images 110 (or parts of images) to each other and/or the map 130, 132 can aid in determining regions to add to the map.

FIG. 2 illustrates determination of a region to be added to a map of a surgical site. FIG. 2 shows an added region 250 which can be a region of an image 110 which is added to a map 130. The added region 250 may be, for example, a previously unmapped region 260. For example, unmapped region 259 is imaged by the device 100, such that one or more of the images 110 includes the unmapped region 259. The device 100 can determine that the region 259 is unmapped and/or that the new image 111 includes an unmapped region(s) 259. The device 100 can then determine to add the region as an added region 250 to the map 130 e.g. as a previously unmapped region 260. Alternatively/additionally, by comparing images 110 to the map 130, similar and/or matching regions can be identified. When an image 110 includes a similar/matching region to a previously captured region of the map 130 and another unmatched region, the unmatched region can be added to the map 130, e.g. to extend the map 130 to previously unmapped areas.

In another example, the added region 250 can be at a different resolution 262 of a previous resolution 261 of a region of the map 130. For example, it can be useful to provide higher resolution data for a region of the map, e.g. when the region is imaged at a higher resolution than previously. In another example, the added region 250 can be at a different focus 272 than a previous focus 271. For example, it is possible to provide sharp images of the surgical site 120 at different depths, e.g. when high magnification is used which may reduce depth of field.

The added region 250 can be at least one of: a previously unmapped region 260, a different resolution 262 than a previous resolution 261 of the map 130, or a different focus 272 than a previous focus 271 of the map 130. Alternatively/additionally, the added region 250 can be an updated image acquired from the device 100. For example, during the surgery a region can change appearance, and it is useful to be able to update the map 130. Alternatively/additionally, the device can acquire an image (e.g. of a region including possibly a region that is already mapped) at a changed focus or changed zoom. The device 100 can subsequently update the map 130 using the updated image acquired at the changed focus and/or zoom.

The device 100 can select the added region 250 from the images 110. Alternatively/additionally, the added region 250 can be selected from a portion of any image 110. It can be advantageous for the added region 250 to be selected such that the map 130 can have more coverage of the surgical site 120, e.g. without needlessly replacing previously mapped regions.

FIG. 3A shows a method of imaging for surgery. The method 300A can include acquiring 310 a plurality of images 110 of a surgical site 120 with the device 100, stitching 320 a map 130 of the surgical site 120 using the plurality of images 110; and outputting 330 (such as for display) the map 130 and/or a real-time image 140 acquired by the surgical device 100.

FIG. 3B shows a method of imaging for surgery. The method 300B can include comparing 313 the added region 150, 250 of the plurality of images 110 to the map 130 before identifying 316 the added region 150, 250 of the plurality of images 110 as being unmapped. The method 300B includes identifying 316 the added region 150, 250 of the plurality of images 110 as being unmapped, and subsequently adding 319 the added region 150, 250 to the map. In the context of FIG. 3B at least, "unmapped" can mean for example a new region (e.g. previously unmapped, e.g. previously unmapped position(s)), new resolution (e.g. previously unmapped at the new resolution), and/or new focus (e.g. previously unmapped at the new focus position).

The method of imaging can include repeatedly comparing, identifying, and adding one of a plurality of added regions to the map. Each of the added regions can be from the plurality of images 110, e.g. including the new and/or real time image 111, 140.

Alternatively/additionally, the method 300B can include, e.g. when comparing 313, identifying regions of similarity of image(s) and the map. For example, a new and/or real time image 111 can include a region that overlaps the map and an unmapped region that can be added 319 to the map. It can be advantageous for the device 100 to have the capability of continuously updating and/or adding to the map 130 to better provide a more complete, higher resolution, or updated map of the surgical site 120.

FIG. 4 illustrates a device output. The output 400, which can be transmitted to one or more displays 135, can include a map 430 and/or real time image 440. The output 400 can include the current location 431, e.g. the current field of view, or center thereof, of the detector 101. The device 100 can be configured to store a position, e.g. a stored position 432, which may be a user determined stored position. The output 400 can include a position label 432L, e.g. to mark the position of the stored position 432. Surgeons and other medical professionals can find stored positions useful such as when desiring to return to a location of the surgical site. the stored position can allow for the surgeon to conveniently know where to return to a site of interest within the surgical site 120. In another example, the stored position 432 can be significant for being a position where a tissue sample is taken, or for corresponding to a feature from a pre-op image, a location of a pre-op image, or where a pre-op image was taken.

For example, the device 100 can allow the storing of a stored position 432 of the map 130, e.g. based on user input. The map 130 and/or real-time image can be marked based on the stored position 432, e.g. with the position label 432L. A surgeon may elect to mark a position as being of interest, e.g. to mark where a biopsy is performed. A marker may alternative/additionally indicate a position of interest for the surgery. In another example, the stored position 432 may be of interest for being associated with a pre-operative image. A surgeon or other medical professional may associate a pre-operative image, tissue sample, and/or surgical procedure with the stored position 432. Labelling of the position 432 can be done with a user selected label. Labels may aid surgeons and other medical professionals in identifying positions of particular significance or interest in the surgical site 120.

User input can be with a mouse, button, audible command, and/or footpedal, for example.

For example, when a surgeon or other user finds a position of the surgical site 120 to be of interest, the user can cause the device 100 to store the position (e.g. as a stored position 432). The stored position 432 can also have a corresponding time stamp in a video record of the surgery. The time stamp can mark the beginning of a scene, e.g. when the video is divided up into a sequence of scenes.

The device 100 can output a marker 450, e.g. for display with the real-time image 440, that indicates the direction and/or distance to the stored position 432, e.g. the direction/distance from the current position 431 to the stored position 432. Surgeon's orientation and ability to return to a previously marked or noted site of interest (e.g. a stored position) can be aided when there is information readily available to point toward the stored position (and/or to indicate the distance to the stored position).

It is possible to mark the map 430 or the real time image 440 with a pointer or marker 450 to indicate at least one of a direction and a distance to the stored position 432. The device 100 can provide the real time image 440, for example, with the marker 450 which may indicate the distance/direction to the stored position 432. The marker 450 can be displayed at an edge 460 of the real time image 440. FIG. 4 shows the current position 431, e.g. where the real-time image 460 is acquired within the map 430. The marker 450 in the real time image 460 can indicate the distance from the center or edge of the field of view of the live image 460 (e.g. acquired from the current position 431 shown in the map 430) to the stored position 432.

for example, the size of the marker may scale with the distance from the current position 431 to the stored position 432 (e.g. the bigger the distance, the larger the marker 450 up to a maximum size). Alternatively/additionally, a value such as a value in millimeters or centimeters or the like can be displayed in the real-time image 440 and/or map 430.

The edge of the real-time image can be a particularly convenient location to put the marker 450 because the position is at the periphery of the main part of the live image, e.g. without obscuring much of the field of view. The edge is also convenient because much of the surgeon's attention is already on the live image. The marker 450 can be located at the edge 460 in such a way as to point toward the stored position 432, which may also aid in intuitively and rapidly informing the surgeon of the direction/distance to the stored position 432.

The output 400 can be displayed, e.g. such that the map 430 is shown as a picture-in-picture, e.g. the map 430 is shown in picture in picture format in the real time image 440. Picture-in-picture can be an advantageous format because it can allow the surgeon to see the real-time image 140 while being oriented within the larger surgical site 120.

FIG. 5 illustrates an added region and associated parameters. The map 130, 430 can include associated parameters, such as parameters associated with regions of the map. As shown in FIG. 5, parameters 555, which can be associated with a map 130, 430 and/or added region 550, can include position 555*a*, focus setting(s) 555*b*, and/or zoom setting(s) 555*c*, for example. For example, the zoom and/or focus settings, e.g. of the imaging device 100, can be used to determine parameters 555 of added region(s) 550. The parameters can alternatively/additionally include a dimension of the added region(s) 550. Including parameters to associate with different regions can provide useful data for generating the map 130. For example, position parameters 555*a* can aid in determining the relative positions of different regions or depths of the map. Zoom 555*c* and/or focus 555*b* related parameters can aid in determining relative heights of features.

FIG. 6 illustrates a stack of images. A stack 600 can be a group of images taken at the same position. The stack 600 can include multiple images where the focus is at different focal planes, such as a first focal plane 601, second focal plane, and/or third focal plane 603. Stacks 600 of images can be included in the map 130, 430 and/or region(s). Portions of images from stacks 600 may alternatively/additionally be used in the map 130, 430 and/or regions. For example, stacks 600 can be used to improve the resolution of a map 130, 430 at position(s) where there may be relatively large changes in the height of the surgical site 120. At high magnification, the depth of field can be reduced so that a single image at a single focal distance does not produce an image with the entire field of view in focus due to changes in height beyond the depth of field. Stacks 600, or at least portions thereof, can be used to improve the image and/or map resolution, particularly for the case of significantly large changes of height within a field of view of the detector 101, e.g. height differences within the field of view which are at or above the depth of field of the detector 101. Stacks 600 can be useful for determining height information in the map and/or for providing better resolution at different heights.

It is furthermore contemplated that the map 130, 430 can be a three dimensional map. It is possible that movements of the detector 101 and/or subject can allow for the stitching together of a map that includes regions of images taken at different x, y, and z positions. Acquiring images at different focuses can allow for stitching of images along the z-direction. Including the z direction as an additional parameter (e.g. in addition to positions x and y) may allow for maps with greater depth of field, for example. This can be particularly advantageous when the a region and/or field of view includes relatively high variability of depth, e.g. structures that extend beyond the normal depth of field provided by the detecting optics. Alternatively/additionally, acquiring images at variable zoom settings (zooming along z) can provide greater resolution (e.g. when zoomed in), and/or provide a larger area image (e.g. when zoomed out).

FIG. 7 illustrates a device for providing a video of a surgery. The device 700 can output a map 730 of a surgical site, e.g. for display. The device 700 can output a line 710 for display on the map 730, the line 710 connecting positions 701, 702, 703 on the map 730. The positions 701, 702, 703 can correspond to respective scenes of a video of a surgery of the surgical site 120. The map 730 can be provided in addition to an output corresponding to the recorded video of the surgery. The map 730, line 710, and positions 701, 702, 703 can aid an intuitive understanding of the surgical processes that was recorded in the video. A surgeon or other medical professional can look at the map 730, line 710, and positions 701, 702, 703 and quickly realize the spatial and/or temporal progress of the surgical procedure that was recorded.

FIG. 8 illustrates a video. The video 800 can include one or more scenes, such as first, second, and third scenes, 801, 802, 803. Each scene 801, 802, 803 has a first frame 801*a*, 802*a*, 803*a* of the respective scene 801, 802, 803. Each first frame 801*a*, 802*a*, 803*a* can be the first frame of a plurality of sequentially recorded frames of a respective scene 801, 802, 803. (The video 800 can include a sequence of frames which can be divided into scenes 801, 802, 803, each scene being a portion of the video 800.) It can be convenient that the scenes 801, 802, 803 are linked to the positions 701, 702, 703 and/or timestamps 761, 762, 763 by the first frames 801*a*, 802*a*, 803*a*, for example.

The map 730 can be provided as an output by the device 700 in addition to an output corresponding to the video 800 of the surgery. The device 700 for providing the video of the surgery can be combined with the surgical imaging device 100.

The positions 701, 702, 703 of the map 730 can correspond to the respective scenes 801, 802, 803. For example, a first position 701 can be where the first scene 801 is recorded; a second position 702 can be where the second scene 802 is recorded; a third position 703 can be where the third scene 803 is recorded. It can be convenient that the scenes 801, 802, 803 of the video 800, timestamps 761, 762, 763, and/or positions on the map are stored so that there is a correspondence between them, e.g. so that a user can better intuitively understand the temporal and spatial parts of the surgical procedure that is recorded.

The device 700 can output a timeline indicator such as timeline bar 740, as shown in FIG. 7. The timeline bar 740 may have indicators to indicate timestamps 761, 762, 763, which may correspond to the respective positions 701, 702, 703. The timeline bar 740 can particularly aid in a user's intuitive understanding of the temporal and spatial parts of the recorded surgical procedure.

Scenes 801, 802, 803 may be recorded at respective positions 701, 702, 703. Alternatively/additionally, the scenes 801, 802, 803 may be associated with respective positions 701, 702, 703; e.g. the scenes 801 may at the respective positions 701, 702, 703 but allow for some movement of the detector 101 so that a given scene is not necessarily completely recorded at the exact same position. In another example, the position(s) 701, 702, 703 can be the average position for a given respective scene.

In another example, one or more scenes can be recorded at the same position. For example, a first scene at a given position can pertain to a first part of the surgical procedure, such as accessing a site of a lesion. A subsequent scene may be recorded at the same position, and pertain to removal/ treatment of the lesion. A yet further subsequent scene at the same position may pertain to preparing the site for an implant. A yet further subsequent scene at the same position may pertain to implanting the implant.

The timeline bar 740 can indicate the timestamps 761, 762, 763 to mark respective scenes 801, 802, 803, such as the first frames 801a, 802a, 803a thereof.

A slider 750 can be provided to be associated with the time bar 740. For example, the slider 750 can indicate the playback position of the video 800. The slider 750 may allow for user input to select a position of the timestamps 761, 762, 763 and/or positions 701, 702, 703 which may correspond to the respective timestamps 761, 762, 763.

A marker 755 can be provided to be associated with the line 710 and/or positions 701, 702, 703. The positions 701, 702, 703 can be labeled, e.g. labeled on the map 730. As shown in FIG. 7, the labels are circles at respective positions 701, 702, 703 on the map 730. The device 700 can receive a user selection of one of the positions 701, 702, 703, for example, by moving the marker 755 (e.g. to a label at a selected position of the positions 701, 702, 703). The user selection of one of the positions 701, 702, 703 can cause the corresponding scene 801, 802, 803 to begin playing; the scene to play can correspond to the corresponding scene of the selected position (beginning at the first frame of the scene corresponding to the selected position). Providing the user with the marked positions 701, 702, 703 for selecting the scene 801, 802, 803 to begin playing can be convenient and intuitive for the user, for reviewing a recorded surgery. It can aid in allowing users to reach desired portions, or scenes, of the surgery. Alternatively/additionally, the line 710 can provide an intuitive aid to understanding how to reach the different portions, or scenes, of the video 800, as a guide to the temporal and/or spatial path taken by the surgeon during the surgery.

The label(s) at position(s) 701, 702, 703 can correspond to a respective frame 801a, 802a, 803a for the video 800. The labels can be displayed on the map 730, e.g. at positions 701, 702, 703. Any label can be selected by the user for playing the video 800 beginning at the corresponding frame which corresponds to the position indicated by the label.

Alternatively/additionally, the timeline bar 740 can have a slider 750 associated therewith. The slider can indicate the time elapsed/remaining in the video 800. Alternatively/additionally, the slider 750 can for user input for selecting a frame and/or scene of the video 800 for beginning playback. The slider can aid in allowing users to reach desired portions, or scenes, of the surgery.

The marker and/or slider can move to a subsequent position/scene when the surgical recording finishes playing a scene and begins playing a subsequent scene.

The device 700 can sequentially display frames of the surgical recording (e.g. the video), which include one or more scenes 801, 802, 803. Each scene 801, 802, 803 can be associated with (e.g. recorded at) a corresponding position 701, 702, 703 of a surgical site 120. The map 730 can be displayed by the device 700 or the map 730 can be output for display by the device 700. The line 710 can be displayed on the map, the line 710 connecting the positions 701, 702, 703, which, as noted above, can correspond to scenes 801, 802, 803. The marker 755 can be displayed on the line 710. User input can be received which moves the marker 755 on the line to a selected position corresponding to a selected scene of the scenes 801, 802, 803. The recording/video can be played beginning at a first frame of the selected scene.

The first frames 801a, 802a, 803a of scenes 801, 802, 803 can be determined by at least one of: a change of the field of view of the video 800, a change of the field of view of the surgical imaging device 100 (e.g. when the device is moved to a different region of the surgical site 120), or a user input (e.g. a command to generate a timestamp 761, 762, 763 and/or begin a scene). A corresponding label can be added/provided to each scene 801, 802, 803, the label(s) possibly being determined by at least one of: a timestamp, a duration of the scene, or a user input. The map 730 can be labeled with the labels which indicate the scenes 801, 802, 803 and/or positions 701, 702, 703. In the example of FIG. 7, the labels can be regarded as the reference numerals 701, 702, 703 which indicate positions 701, 702, 703, which have respective corresponding time stamps 761, 762, 763 and scenes 801, 802, 803.

Figures 9, 10:
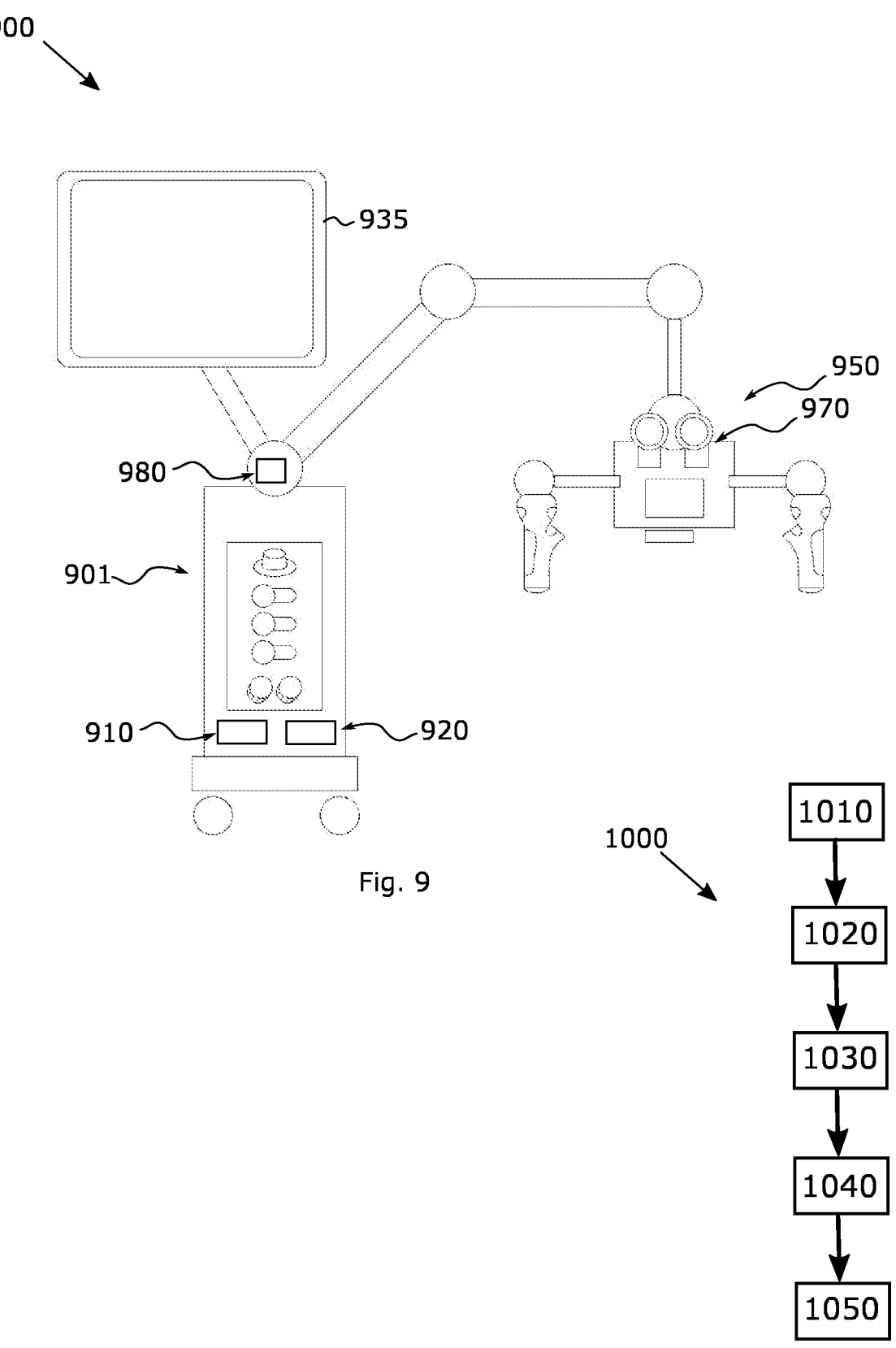
FIG. 9 illustrates a surgical imaging device, according to embodiments described herein.
FIG. 10 illustrates a workflow, according to embodiments described herein.

FIG. 9 illustrates a surgical imaging device. The surgical imaging device 900 of FIG. 9 may be referred to as a system, e.g. a system including a computer and an imaging device. The surgical imaging device 900 may include a computer device (e.g. personal computer, laptop, tablet computer or mobile phone) with one or more processors 910 and memory 920 (which may include one or more memory devices). The memory 920 can be located in the computer device or be in a distributed computing system (e.g. cloud computing system with the one or more processors 910 and one or more memories 920 distributed at various locations, for example, at a local client and one or more remote server farms and/or data centers). The surgical imaging device 900 may include a data processing system that includes a system bus to couple the various components of the surgical imaging device 900. The system bus may provide communication links among the various components of the surgical imaging device 900 and may be implemented as a single bus, as a combination of busses, or in any other suitable manner.

An electronic assembly may be coupled to the system bus. The electronic assembly may include any circuit or combination of circuits. In one embodiment, the electronic assembly includes a processor which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA) of the microscope or a microscope component (e.g. camera) or any other type of processor or processing circuit. Other types of circuits that may be included in electronic assembly may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The surgical imaging device 900 can include one or more memories 920, which in turn may include one or more memory elements suitable to the particular application, such as a main memory in the form of random access memory (RAM), one or more hard drives, and/or one or more drives that handle removable media such as compact disks (CD), flash memory cards, digital video disk (DVD), and the like.

The surgical imaging device 900 may also include a display 935, one or more speakers, and/or a keyboard and/or controller, which can include a mouse, trackball, touch screen, voice-recognition device, or any other device that permits a system user to input information into and receive information from the surgical imaging device 900.

Additionally, the surgical imaging device 900 may include a microscope 950 connected to a computer device or a distributed computing system. The surgical imaging device 900 can include a detector for acquiring data for images.

Additionally, the surgical imaging device 900 may include a microscope connected to a computer device or a distributed computing system. The microscope may be configured to generate biology-related image-based input training data by taking an image from a biological specimen.

Herein, a microscope may be a light microscope (e.g. diffraction limited or sub-diffraction limit microscope as, for example, a super-resolution microscope or nanoscope). The microscope may be a stand-alone microscope or a microscope system with attached components (e.g. confocal scanners, additional cameras, lasers, climate chambers, automated loading mechanisms, liquid handling systems, optical components attached, like additional multiphoton light paths, lightsheet imaging, optical tweezers and more). Other imaging modalities may be used as well, such as modalities for imaging objects related to tissues, biological specimens, and the like (e.g. proteins, nucleic acids, lipids).

FIG. 9 also shows a detector 970, which may be a camera, for acquiring images from the surgical site 120. The detector 970 can be part of a surgical imaging device such as a microscope 950 as shown.

FIG. 9 illustrates an image processing device 901 coupled to a microscope 950. An image processing device 901 may include a processor 910, e.g. a computer processor. The imaging device (e.g. surgical imaging device 900) can be communicatively coupled to memory and/or include an internally located memory 920. The device 901 can have a display 935, or provide an output for display. The image processing device 901 can be coupled to (or be part of) a surgical imaging device 900. The image processing device 901 can be coupled to a microscope 950, for example. An image processing device 901 and imaging apparatus such as a microscope 950 can form a surgical imaging device 900.

An image processing device, such as the image processing device 901 shown in FIG. 9, can function as a device for providing playback of a video of a surgical procedure. The surgical imaging device 900 can acquire images and output data for display, such as is described herein. Alternatively, the surgical imaging device 900 can include a display 935 so that the device 900 is capable of displaying images. Images for display can include the real-time image of the surgery (e.g. the live image acquired by the detector 970), the recorded video of the surgery, and/or the map.

The processor 910 can be used to perform the methods described herein, such as methods of imaging processing, determining a map using images, stitching together a map using images. comparing regions of images and/or maps, identifying regions as being unmapped or previously mapped, and/or adding regions of images to a map.

For example, during surgery, the image processing device 901 can be communicatively coupled to a surgical instrument such as a microscope 950 that can include the detector 970 (e.g. a camera). As shown in FIG. 9, the surgical instrument can be a microscope 950, e.g. a surgical microscope. The surgical instrument may be another type of imaging device such as an ultrasound device, optical coherence tomography device, or camera.

The image processing device 901 can include a memory storage device 920 and/or be coupled to external memory (e.g. one or more memory devices). Images/image data can be accessed in local and/or remote memory, for example. The processor 910 (which can have multiple cores and/or multiple processors) can be used for image processing. The image processing device 901 can determine the map 130, for example, e.g. by adding regions to the map 130.

One or more sensors 980 for determining the position/orientation of the detector 970 and/or image(s) 110 may be employed. The sensors 980 may aid in determining the relative positions of acquired images 110, which may aid in determining how to stitch an image or portion thereof to the map. For example, accelerometer(s) can determine motions of the detector 970. Camera(s) such as 3D camera(s) can be employed to track/record positions of the imaging apparatus, microscope, detector 970. For example, optical, electrical, electromechanical, and/or optomechanical sensors can be employed to record the relative positions of the booms, arms and any other movable mechanical components for positioning the surgical imaging device 900 and/or field of view thereof. Sensors 980 may be part of the surgical imaging device 900 and/or be communicatively coupled thereto.

The devices and methods described herein can aid in orienting surgeons and other medical professionals during surgery. Alternatively/additionally, the devices and methods herein can aid medical professionals, students, and the like in navigating through a recorded video of a surgery, e.g. for educational purposes. For example, surgeons often move the field of view (e.g. that of an imaging microscope) around to optimize the view to carry out the surgery. Particularly in microsurgery, it can be challenging to keep track of the relative position of different sites of the surgery. Quite often surgeons can interrupt the current action in order to react to something else happening, e. g. attending a sudden hemorrhage in a near location. After attending to the hemorrhage, for example, the surgeon may need to find the previous position, which can take time and effort, lengthening the procedure, and potentially impacting patient outcome.

Herein are described methods and devices that can improve the ability of the surgeon to move the microscope back into desired positions, possibly without a robotic arm. Herein are described the generation/use of maps, e.g. maps of the operating field, which can be assembled, e.g. by a computing unit (e.g. software). It is alternatively/additionally possible to constantly update and/or expand the map, e.g. by using the live images coming from the detector. It can be advantageous to reduce the time needed for the whole surgical procedure. Another advantage can be to increase the confidence of surgeon and the ability to swiftly deal with interruptions and quickly return to a previous position. Another advantage can be to gain additional information about the tissue and location of anatomical landmarks. For example, the ability to mark/store certain locations of the map, and associate information thereto, can aid in providing more information to the medical professionals about the surgery.

Herein, the acquired images can be stereoimages. For example, it is possible for the map to be a stereoimage map. A first map can be made using images from a first perspective (e.g. a first detector) and a second map can be made using images from a second perspective (e.g. a second detector). The first and second maps can be used to generate a stereoscopic map.

Herein, the generation of the map may use a comparator which can check when an acquired (e.g. new) image, frame, or portion thereof, has content different from previous content. A stitching module can be called to combine the image, frame, or portion thereof with the map. The process can be repeated, generating a larger map for example. The map can be displayed on a large screen, e.g. showing a larger area than the area of the real-time image, e.g. the image viewed through the eyepieces of the microscope. A module such as the stitching module can detect changes of magnification. For example, the map can be generated/changed to have varying resolution, e.g. depending on the resolution of the acquired images.

For example, if a region of the surgical site 120 is imaged a subsequent time (e.g. after being included in the map), the map can be updated with a subsequent image or portion thereof, potentially also with higher resolution (e.g. from a subsequent image taken at a higher magnification).

Another functionality described herein is the ability to place markers. In FIG. 4, for example, the position label 432L can be regarded as a type of marker. Alternatively/additionally, the markers described herein may be regarded as a type of position label 432L. The positions 701, 702, 703 of FIG. 7 may be regarded as having a type of position label and/or marker, as described herein.

For example, markers can be placed in the map and/or the in the real-time image. The markers can label positions (e.g. anatomical landmarks) within the surgical site, real and/or map. For example, a marker can be placed so provide a guide to a position which a surgeon expects to return later in the surgery, after moving to a second location. Markers can be placed during surgery or can be placed after the surgery. It may be possible to edit the map associated with a video of a surgery, e.g. to add/edit markers.

Marker(s) can be displayed via overlay onto the real time image and/or map. The markers can be visualized within the view (e.g. as label important spots (anatomical landmarks) within the surgical scene, e.g. to mark where the surgeon may desire to return at different times of the surgical procedure. The marker(s) can be visualized within the users view (either as augmented binocular view or on screen), e.g. as a symbol such as an arrow; multiple colors can be used as well to differentiate individual markers. Users may be able to choose the form and/or color of the symbol used as the marker(s).

Markers can be labeled (such as via commands) to mark different types of positions. For example markers may indicate the position of a surgical device such as a clip, or mark an edge of a tumor, anatomical structure, or the like. Markers and corresponding labels can also be imported from surgical planning tools such as software tools. It is possible to import a list of positions into a map. For example, the devices described herein 100, 901 can allow for importing positions and/or data from an external device. For example, during surgery, a surgeon can can link data from import markers that indicate the position If a marked position is located outside the real time image, then a corresponding symbol, marker, and/or label) can be placed at the edge of the screen, image, display, map, and/or real time image. FIG. 4 illustrates a marker 450 that is at the edge 460 of the real time image 440 indicating that the corresponding marked location is located to the right side of the currently shown (live) position. A marker, such as marker 450 can indicate the position and the distance of the marked location in relation to the current position, e.g. the current center of view. The surgeon can e given guidance as to how to move the imaging device such as the microscope/exoscope to return to the marked position (e.g., referring to FIG. 4, to return to position 432 from current location 431).

The relative distance of stored positions, which have corresponding markers, from the current position can be indicated by the relative size of the symbol or by adding another indicator such as a scale bar or an actual distance value (e.g. in mm) placed at the edge 460. The user can possibly turn on and off the overlay showing the markers (and optionally any associated annotation).

The surgical imaging device can include sensors (e.g. gyroscopes, position sensors, and/or cameras for sensing position), a calibrated zoom assembly, and/or a calibrated focus assembly which can provide data for determination of the position and/or orientation of the detector, (and/or the perspective of the real time image). Such sensors and/or calibrated assemblies can aid in more accurately stitching regions to the map. For example, data from position/orientation sensors which is associated with a captured image(s) can aid in determining where the captured image(s)_is expected to overlap with the map and/or another captured image(s). Alternatively/additionally, the computational burden of stitching regions to the map, and/or determining the map, can be reduced by using sensors (e.g. gyroscopes, accelerometers, movement sensors, position sensors, and/or cameras for sensing position), and/or calibrated zoom/focus assemblies. Positions sensors, accelerometers, and other sensors mentioned herein may aid, similarly, such as by determining movement of the detector, the position of the detector, and/or field of view of the detector, real time image, and/or captured image.

Alternatively/additionally, the surgical imaging device can include or be communicatively coupled to a 3D position detection apparatus. The 3D position detection apparatus can include stereo cameras and/or utilize fiducial markers to track the position of the surgical imaging device.

In another example, combinable with the other examples described herein, the surgical imaging device can use actuators that may have calibrated movements, generating data that can be used to determine the position of the field of view, detector, and/or surgical imaging device. Robotic movements and/or actuators may aid in accurately stitching together images from different locations into the map.

The map can utilize images taken at different focuses and/or zooms to increase resolution particularly for regions where there is a significant range of heights, e.g. heights comparable to the depth of field of the imaging device and/or optics. To the surgeon, it can be an advantage to be able to see more of the map/image in focus. For example, when working in cavities, there may be significant changes in height, which may be at or beyond the depth of field of the optics and/or imaging device. It is possible to sequentially acquire images of the field of view and/or surgical scene and produce an extended depth of focus image from the field of view and/or surgical scene. Viewers can possibly see the entire scene with sharp contrast and detail. Referring to FIG. 6, the use of stacking can aid in providing extended depth of focus, particularly in regions of the surgical site having relatively large height differences, e.g. comparable or greater than the depth of field.

For example, the focus can be swept along the optical axis to acquire a set, or stack, of images. Each part of the field of view can be in focus at least in one of the images of the stack. for subsequent. A fast acquisition can prevent latency issues, such as lagging. Using relatively fast elements in the surgical imaging device, such as an acquisition module thereof, such as liquid lenses and/or deformable mirrors may be used. Such elements can increase the speed of acquiring stacks of images, for example. Liquid lenses and/or deformable mirrors may enable fast change of focus, to reduce latency problems.

FIG. 10 illustrates a workflow, according to embodiments described herein. As shown in the workflow 1000, the imaging device can be moved 1010. The device can stitch 1020 images to a map, e.g. forming a larger map of the surgical field. The user 1030 can mark a position of the map and/or real time image. The imaging device can output or display 1040 the marked position(s), e.g. using image augmentation. The imaging device can be moved 1050 to a new position or a previously marked location. The imaging device can guide movements such as by providing updatable markers. For example, referring to FIG. 4, a marker 450 can be updatable to show the direction and/or distance from the current location 431 to the stored position 432.

For example, the surgical imaging device can stitch images to the map, independent of the zoom and/or magnification of the acquired images. Sensors and/or external devices can be used to improve the precision of the determination of the position of images and/or the detector, for example. Position information may be useful in accurately and/or rapidly stitching new regions to the map.

Herein the methods and devices can be used for tracking movements during surgery. For example, it may be possible to analyze the efficiency of a surgery by tracking. Markers on the timeline bar 740, for example, can be generated to coincide with movements of the field of view of the real time image and/or the detector. For example, movements greater than a threshold movement can be outputted, e.g. in the form of markers on the timeline bar and/or positions on the map.

Some or all of the method steps described herein may be executed by (or using) a hardware apparatus, like for example, a processor, a microprocessor, a programmable computer or an electronic circuit.

The methods described herein can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. The digital storage medium may be computer readable.

Some embodiments according to the invention include a data carrier having electronically readable control signals, which are capable of cooperating with a programmable computer system, such that one of the methods described herein is performed.

Embodiments described herein can be implemented as a computer program product with a program code, the program code being operative for performing one of the methods when the computer program product runs on a computer. The program code may, for example, be stored on a machine readable carrier.

Other embodiments include the computer program for performing one of the methods described herein, stored on a machine readable carrier.

Herein is disclosed a computer program having a program code for performing the methods described herein, when the computer program runs on a computer.

Herein is disclosed a storage medium (or a data carrier, or a computer-readable medium) comprising, stored thereon, the computer program for performing the methods described herein when it is performed by a processor. Herein is disclosed an apparatus as described herein comprising a processor and the storage medium for executing the methods described herein.

Herein is disclosed a data stream or a sequence of signals representing the computer program for performing one of the methods described herein. The data stream or the sequence of signals may, for example, be configured to be transferred via a data communication connection, for example, via the internet.

Herein is disclosed a processing means, for example, a computer or a programmable logic device, configured to, or adapted to, perform the methods described herein.

Herein is disclosed a computer having installed thereon the computer program for performing the methods described herein.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. The methods described herein are preferably performed by any hardware apparatus.

Herein, a "map" can refer to at least one image which can provide a visualization, e.g. a visualization of a surgical site. A map can be a combination of multiple individually received/collected images. The map can be a visual representation of at least a part of a surgical site. The map can be stored by computer memory and/or displayed, in whole or in part, by a display. Herein, a map can be formed by stitched images.

Herein "stitching" can refer to combining multiple images together. Stitching can combine images which have overlapping regions and/or overlapping fields of view. Stitching can generate a resultant image which includes image data from any two or more of the component images which are stitched together to generate the resultant image. The resultant image may provide an image/map of a region which is larger than the individual regions of the images which are combined. Alternatively/additionally, stitching can provide a resultant image which has greater resolution and/or depth of field than the individual images which are combined.

Herein an "imported position" can be a position which is received by any of the devices described herein (the device 700, or surgical imaging device 100, 900). The imported position can come from user input and/or a communicatively coupled external device. In an example, data from images taken from another imaging modality can be used to determine positions for marking. For example, an imported position can be an anatomical position and/or position of a tumor. The imported position can have been determined previous to the surgical procedure being recorded, and possibly imported during the surgical procedure. In another example, the imported position can be imported after the surgical procedure, such as during playback of the video of the surgical procedure. Imported positions may also have labels associated therewith, e.g. for explanation of the significance of the position (e.g. position of a tumor and/or resection). Imported positions may aid in the navigability of the video, e.g. by providing additional information or context for scenes of the video.

Herein is disclosed the following enumerated examples of methods which can be executed by any of the surgical imaging devices described herein. Alternatively/additionally, a computer program may include instructions for executing the following enumerated examples.

Example 1 is a method of imaging for surgery, comprising: acquiring a plurality of images of a surgical site with a surgical apparatus; stitching a map of the surgical site using the plurality of images; and displaying the map and a real-time image acquired by the surgical apparatus.

Example 2 is like example 1, wherein stitching includes adding an added region to the map, wherein the plurality of images includes the added region. The total field of view of the plurality of images can include the added region.

Example 3 is like example 2, wherein the added region is at least one of: a previously unmapped region, a different resolution than a previous resolution of the map, or a different focus than a previous focus of the map.

Example 4 is the method of any preceding example, further comprising acquiring new images, in real time, to add to the plurality of images.

Example 5 is any one of examples 2-4, further comprising: selecting the added region from the plurality of images.

Example 5.1 is the method of any one of example 2-5, further comprising: comparing the added region of the plurality of images to the map before identifying the added region of the plurality of images as being unmapped, identifying the added region of the plurality of images as being unmapped, and subsequently adding the added region to the map. An unmapped region can be a new region in space, new resolution, and/or new perspective (angle)]

Example 5.2 is the method of imaging of any one of examples 2-5.1 example, further comprising: repeatedly comparing, identifying, and adding one of a plurality of added regions to the map, wherein each of the added regions is from the plurality of images.

Example 6 is the method of imaging for surgery of any preceding example, further comprising: updating the map using an updated image acquired from the device.

Example 7 is example 6, further comprising: acquiring at a changed focus or acquiring at a changed zoom, and subsequently, updating the map using the updated image acquired at the changed focus or changed zoom. The updated image can be acquired at a different resolution, focus, perspective, angle, or zoom of a part the map.

Example 8 is the method of imaging for surgery of any preceding example, further comprising: storing a position of a point of the map based on a user input; and marking at least one of the map or the real time image based on the position.

Example 9 is the method of example 8, further comprising: associating a pre-operative image with the position, such as based on user input.

Example 10 is the method of imaging of example 8 or 9, further comprising: labeling the position with a user selected label.

Example 11 is the method of imaging of example 8, 9, or 10, further comprising: marking the map or the real time image with a marker or pointer to indicate at least one of a direction and a distance to the position. The distance can be from the center or edge of the field of view of the real time image to the position.

Example 12 is example 11, wherein the pointer is displayed at an edge of the real time image.

Example 13 is any preceding example, wherein the displaying is displaying the map as a picture-in-picture of the real-time image.

Example 14 is any one of examples 2-13, further comprising using zoom settings or using focus settings to determine parameters of the added region; wherein optionally the parameters include at least one of a position of the added region in the map, or a dimension of the added region.

Example 15 is any preceding example, wherein acquiring the plurality of images includes: acquiring a stack of images at different focuses at a given position.

Examples 16-20 can be in regard to user interface and/or device that is used for playing the video of a surgery, e.g. an image processing device configured as described in the examples.

Example 16 includes a displayed map of a surgical site, a line on the map which connects a plurality of positions on the map, wherein the positions each correspond to respective scenes of a video of a surgery of the surgical site. The video can include a sequence of frames which each may have a corresponding timestamp.

Example 17 is example 16, wherein each scene includes a first frame which is the first frame of a plurality of sequentially recorded frames at the position corresponding to the scene.

Example 18 is example 16 or 17, configured to receive a user selection of a selected position of the plurality of the positions, and play the recording beginning at a first frame of the scene which corresponds to the scene corresponding to the selected position.

Example 19 is any one of examples 16-18, further comprising a label at one of the positions, wherein the label corresponds to a frame of the recording, wherein the label is displayed on the map, and the label is selectable by the user for playing the recording beginning at the frame of the recording which corresponds to the label.

Example 20 is any one of examples 16-19, further comprising a timeline bar which is displayed, and a slider, in the timeline bar, wherein the slider is configured for user input for selecting a frame of the recording.

Examples 21-26 are also hereby disclosed, which are methods that can be performed by image processing devices as described herein. A computer program to execute the methods is also contemplated.

Example 21 is a method of playback of a surgical recording, comprising: sequentially displaying frames of a surgical recording which includes a plurality of scenes, wherein each scene is associated with a corresponding position of a surgical site, displaying a map of the surgical site, displaying a line on the map which connects a plurality of positions which correspond to each scene, displaying a marker on the line, receiving user input which moves the marker on the line to a selected position corresponding to a selected scene of the plurality of scenes, and playing the surgical recording beginning at a first frame of the selected scene.

Example 22 is example 21, further comprising: moving the marker to a subsequent scene when the surgical recording finishes playing a previous scene and begins playing the subsequent scene.

Example 23 is a method of recording a surgery, comprising: recording a video with a surgical imaging apparatus, determining a plurality of scenes of the video, each scene having a first frame of a plurality of sequentially recorded frames of the video, the sequentially recorded frames being recorded at a position of a surgical site corresponding to the scene, determining a timeline of the surgery, the timeline including: a sequence of the plurality of scenes.

Example 24 is example 23, wherein the first frame of each scene is determined by at least one of: a change of the field of view of the surgical imaging apparatus, or a user input.

Example 25 is example 23 or 24, further comprising adding a corresponding label to any scene, wherein each corresponding label is determined by at least one of: a timestamp, a duration of the scene, or a user input.

Example 26 is any one of examples 23-25, further comprising the method of imaging of any of examples 1-15, and labeling the map with a plurality of indicators which indicate the scenes.

Although some aspects have been described in the context of an apparatus, it is clear that these aspects also represent a description of the corresponding method. Analogously, aspects described in the context of a method step also represent a description of a corresponding apparatus.

The list of reference signs below is not intended to be limiting.

| List of reference signs | |
| --- | --- |
| 100 | imaging device |
| 101 | detector |
| 110 | images |
| 111 | new images |
| 120 | surgical site |
| 130 | map |
| 131 | current location |
| 131a | region |
| 131b | region |
| 131c | region |
| 131d | region |
| 131e | region |
| 132 | map |
| 135 | display |
| 140 | real time image |
| 141 | real time image |
| 150 | added region |
| 250 | added region |
| 259 | unmapped region |
| 260 | previously unmapped region |
| 261 | previous resolution |
| 262 | different resolution |
| 271 | previous focus |
| 272 | different focus |
| 281 | old |
| 282 | updated image |
| 300 | method |
| 310 | acquire images |
| 313 | compare |
| 316 | identify |
| 319 | add |
| 320 | stitching region |
| 330 | display map and runtime image |
| 430 | map |
| 431 | current location |
| 432 | stored position |
| 432L | position label |
| 440 | real time image |
| 450 | marker (e.g. pointer) |
| 460 | edge |
| 550 | added region |
| 555 | parameters |
| 555a | position |
| 555b | focus |
| 555c | zoom |
| 600 | stack |
| 601 | first focal plane |
| 602 | second focal plane |
| 603 | third focal plane |
| 700 | device |
| 701 | position 1 |
| 702 | position 2 |
| 703 | position 3 |
| 710 | line |
| 730 | map |
| 740 | timeline bar |
| 750 | slider |
| 755 | marker |
| 761 | timestamp 1 |
| 762 | timestamp 2 |
| 763 | timestamp 3 |
| 800 | video |
| 801 | scene 1 |
| 802 | scene 2 |
| 803 | scene 3 |
| 801a | first frame of scene 1 |
| 802a | first frame of scene 2 |
| 803a | first frame of scene 3 |
| 900 | surgical imaging device |
| 901 | image processing device |
| 910 | one or more processors |
| 920 | memory |
| 935 | display |
| 950 | microscope |
| 970 | detector |
| 980 | sensor(s) |
| 1000 | workflow |
| 1010 | move imaging device |
| 1020 | stitch images |

-continued

| List of reference signs | |
| --- | --- |
| 1030 | mark a position |
| 1040 | output or display |
| 1050 | move imaging device |

The invention claimed is:

1. A surgical imaging device, comprising a processor configured for:
    acquiring a plurality of images of a surgical site;
    stitching a map of the surgical site using the plurality of images;
    obtaining a video of a surgery of the surgical site;
    determining a plurality of scenes of the video, wherein each scene has a first frame of a plurality of sequentially recorded frames of the video recorded at a certain position of the surgical site corresponding to each scene;
    inserting a line on the map which connects a plurality of positions on the map, wherein each of the positions corresponds to a respective scene of the video of the surgery of the surgical site;
    acquiring real-time images of the surgical site;
    updating and/or expanding the map by using the real-time images;
    generating display data to display the video or the real time images along with the map including the line; and
    sending the display data to a display device.

2. The surgical imaging device of claim 1, wherein the stitching includes adding an added region to the map, wherein the plurality of images includes the added region, wherein the added region is at least one of:
    a previously unmapped region, a region with a different resolution than a previous resolution of the map, or a region with a different focus than a previous focus of the map.

3. The surgical imaging device of claim 2, wherein the processor is further configured for:
    comparing the added region of the plurality of images to the map before identifying the added region of the plurality of images as being unmapped,
    identifying the added region of the plurality of images as being unmapped, and
    subsequently adding the added region to the map.

4. The surgical imaging device of claim 2, wherein the processor is further configured for using zoom settings or focus settings to determine parameters of the added region, wherein the parameters include at least one of a position of the added region in the map, or a dimension of the added region.

5. The surgical imaging device of claim 1, wherein the processor is further configured for:
    updating the map using an updated image acquired by the surgical imaging device,
    wherein the processor is configured for acquiring the updated image at a changed focus or at a changed zoom, and subsequently, updating the map using the updated image acquired at the changed focus or at the changed zoom.

6. The surgical imaging device of claim 1, wherein the processor is further configured for:
    storing a position of a point of the map based on a user input; and
    marking at least one of the map or the real time image based on the position.

7. The surgical imaging device of claim 6, wherein the processor is further configured for:

associating a pre-operative image with the position.

8. The surgical imaging device of claim 6, wherein the processor is further configured for:

labeling the position with a user selected label.

9. The surgical imaging device of claim 6, wherein the processor is further configured for:

marking the map or the real time image with a pointer to indicate at least one of a direction and a distance to the position.

10. The surgical imaging device of claim 9, wherein the processor is further configured for displaying the pointer at an edge of the real time image.

11. The surgical imaging device of claim 1, wherein acquiring the plurality of images includes:

acquiring a stack of images at different focuses at a given position.

12. The surgical imaging device of claim 1, wherein the processor is configured to receive a user selection of a selected position of the plurality of the positions, and play the video beginning at a first frame of the scene corresponding to the selected position.

13. The surgical imaging device of claim 1, wherein the processor is further configured for:

outputting a label at one of the positions, wherein the label corresponds to a frame of the video, wherein the label is selectable by the user for playing the video beginning at the frame of the video which corresponds to the label.

14. The surgical imaging device of claim 1, wherein the processor is further configured for displaying:

a timeline indicator, and a slider in the timeline indicator, wherein the slider is configured for user input for selecting a frame of the video.

15. The surgical imaging device of claim 1, wherein the processor is further configured for:

outputting a marker for marking the line, receiving user input for moving the marker on the line to a selected position corresponding to a selected scene of the plurality of scenes, and playing the video beginning at a first frame of the selected scene.

16. The surgical imaging device of claim 15, wherein the processor is further configured for:

moving the marker to a subsequent scene when the video finishes playing a previous scene and begins playing the subsequent scene.

17. The surgical imaging device of claim 1, wherein the processor is further configured for:

determining a timeline of the surgery, the timeline including a sequence of the plurality of scenes; and outputting a timeline bar for the timeline of the surgery.

18. The surgical imaging device of claim 17, wherein the first frame of each scene is determined by at least one of:

a change of a field of view of the surgical imaging device, or a user input.

* * * * *